(12) United States Patent
Ertl et al.

(10) Patent No.: US 11,766,177 B2
(45) Date of Patent: Sep. 26, 2023

(54) DENTAL PROBE

(71) Applicant: DENTSPLY SIRONA inc., York, PA (US)

(72) Inventors: Thomas Ertl, Ranstadt-Dauernheim (DE); Naim Karazivan, Repentigny (CA); Alexander Savic, Munich (DE)

(73) Assignee: DENTSPLY SIRONA INC., York, PA (US)

( * ) Notice: Subject to any disclaimer, the term of this patent is extended or adjusted under 35 U.S.C. 154(b) by 170 days.

(21) Appl. No.: 17/337,563

(22) Filed: Jun. 3, 2021

(65) Prior Publication Data

US 2021/0369120 A1 Dec. 2, 2021

Related U.S. Application Data

(63) Continuation of application No. 16/092,046, filed as application No. PCT/EP2017/058453 on Apr. 7, 2017, now abandoned.

(30) Foreign Application Priority Data

Apr. 8, 2016 (EP) ..................................... 16164539

(51) Int. Cl.
 *A61B 5/00* (2006.01)
 *A61B 5/026* (2006.01)
 *A61C 1/08* (2006.01)

(52) U.S. Cl.
 CPC .......... *A61B 5/0088* (2013.01); *A61B 5/0261* (2013.01); *A61B 5/682* (2013.01); *A61B 2562/0238* (2013.01); *A61C 1/088* (2013.01)

(58) Field of Classification Search
 CPC .... A61B 5/1455; A61B 5/0088; A61B 5/0261
 See application file for complete search history.

(56) References Cited

U.S. PATENT DOCUMENTS

| 4,836,206 A | 6/1989 | Maxwell |
| 5,259,761 A | 11/1993 | Schnettler |
| 8,442,609 B2 | 5/2013 | Jenkins |

FOREIGN PATENT DOCUMENTS

DE 19649689 A1 6/1998

OTHER PUBLICATIONS

International Search Report; PCT/EP2017/058453; Jun. 27, 2017 (completed); dated Jul. 4, 2017.

(Continued)

*Primary Examiner* — Marjan Fardanesh
(74) *Attorney, Agent, or Firm* — DENTSPLY SIRONA INC.

(57) ABSTRACT

A dental probe for determining the vitality of a tooth, comprising a light emitter and a light receiver, wherein the light emitter emits light from an emitter surface adapted to be positioned on a hard dental surface of a tooth, wherein the light receiver collects light incident on a receiver surface adapted to be positioned on a hard dental surface of the tooth so that the optical path of the light emitted from the light emitter passes at least through a portion of the pulp chamber of the tooth. The light receiver includes a light shielding spacer member adjacent to the optical path for establishing and maintaining a distance of at least 50 μm between the gum line and the optical path at the receiver surface. The light emitter further a light shielding spacer member adjacent to the optical path for establishing and maintaining a distance between the gum line and the optical path at the emitter surface, wherein the light shielding spacer member establishes and maintains a distance of at least 50 μm between the gum line and the optical path at the emitter surface, and in that an apical-coronal diameter of the light emitter surface and the light receiver surface is at most 1200 μm in the direction normal to the optical path.

13 Claims, 7 Drawing Sheets

(56) References Cited

OTHER PUBLICATIONS

International Preliminary Report on Patentability; PCT/EP2017/058453; Jun. 27, 2017 (completed); dated Jul. 4, 2017.
Written Opinion of the International Searching Authority; PCT/EP2017/058453; Jun. 27, 2017 (completed); dated Jul. 4, 2017.

DENTAL PROBE

THE CROSS-REFERENCE TO RELATED APPLICATIONS

This application is a continuation of U.S. application Ser. No. 16/092,046, filed Oct. 8, 2018 (now abandoned), which is a national phase of PCT/EP2017/058453, filed Apr. 7, 2017.

FIELD OF THE INVENTION

The present invention relates to an optical tooth characterization based on, an objective examination of the pulp of the tooth. Specifically, the present invention relates to a dental probe for determining the vitality of a tooth, in particular of a tooth previously having been restored by a filling, crown or bridge, for example. The dental probe is also useful for determining additional parameters including a bacterial, inflammation, and/or health status by irradiation of light through a portion of the pulp chamber. Accordingly, the present invention allows optical tooth characterization under crowns and other restorations.

Advantageously, the dental probe comprises a light emitter surface and/or a light receiver surface, which may form part of a member adapted to be removably attached to the dental probe. The member adapted to be removably attached to the dental probe may be disposable and/or sterilizable.

The present invention also relates to a disposable and/or sterilizable member for the dental probe comprising the light emitter surface or the light receiver surface. Moreover, the present invention relates to a dental system comprising the dental probe according to the first aspect and a control unit.

The dental probe of the present invention allows the objective and non-invasive determination of the vitality of a tooth, in particular a tooth previously having been restored, for example, by a filling, crown or bridge, with improved specificity and sensitivity due to an enhancement of the signal to noise ratio by specific mechanical measures provided on the probe.

BACKGROUND OF THE INVENTION

Pulp vitality testing is an important aid in the diagnosis of pulp disease and apical periodontitis. Endodontic treatment or even extraction may be indicated in case the pulp is deemed to be severely compromised as a result of the diagnostic testing. Moreover, conservative procedures aimed at preserving pulp vitality, can only be effective if the status of the pulp is accurately assessed. The ideal pulp test should provide a simple, objective, standardized, reproducible, non-painful, non-injurious, accurate, and inexpensive way of assessing the condition of the pulp tissue. Moreover, given that the vitality of a tooth having been restored by a filling, crown or bridge is more likely to be compromised as compared to a previously untreated tooth, the ideal pulp vitality test must be suitable for being carried out on a restored tooth, namely in the presence the restoration. However a restoration such as a filling, crown or bridge is not transparent to light of a wavelength of interest. Therefore, a restoration poses significant problems to any measurement using electromagnetic radiation, in particular when the restoration extends as far as below the gum line.

Accordingly, conventional pulp testing strategies employed most frequently by dental practitioners, involve subjective sensitivity tests such as thermal or electric pulp testing, which correlate a response to a stimulus to the vitality of the pulp. Specifically, a thermal or electric stimulus is applied to the tooth under examination and the patient is asked whether a sensation is felt.

Unfortunately, the sensation can be unpleasant or painful to the patient. Moreover, the successful stimulation of nerves in the pulp does not exclude the possibility of pulp disease. For example, nerves can still respond even when blood circulation is impaired. Furthermore, stimulating a tooth without also stimulating surrounding gingival tissues or nearby teeth is difficult. Finally, no information concerning the degree or type of pulp pathology can be positively identified, except in case of complete devitalization of the pulp. Accordingly, any thermal and the electrical sensitivity tests have a relatively high rate of false positives and false negatives.

For example, in cold thermal testing the dentinal fluid within the dentinal tubules contracts. A rapid outward flow of fluid within the patent tubules thereby generates hydrodynamic forces acting on nerve fibres within the pulp-dentine complex, which is experienced by the patient as a sharp sensation. Although the test may be carried out by a simple and inexpensive procedure, the quality of the results is not ideal. Specifically, the cold test provides a sensitivity of 0.84 which means only a 84% chance of achieving a positive result when individuals with the disease are tested. Moreover, the cold test provides a specificity of 0.93 which means only a 93% chance of returning negative results when performed on persons without the disease.

Accordingly, the cold test gives rise to false positive results where a non-vital tooth appears to respond positively to testing. Therefore, there is a risk that a non-vital tooth is left untreated. Moreover, the cold test may also give false negative results meaning that a vital tooth has not responded positively to testing. As a result, a vital tooth may be subject to an unnecessary and costly endodontic treatment.

U.S. Pat. No. 8,442,609 discloses a device for determining the health of oral objects by providing objective measurements using a detachable probe body. The detachable probe body may isolate reusable system components (including an electromagnetic signal detection, signal transmission, energy generation, and or energy transmitting components) from the oral cavity, optionally by encasing at least a portion of one or more of these components in a sheath or the like. A window of the probe body maintains sterile isolation and transmits electromagnetic energy to and/or signals from the oral object. Accuracy can be enhanced by a clamp or other structure for engaging a surface of the oral object so as to maintain a fixed alignment between the signal receiver and the oral object. The probe body is large as compared to a tooth and cannot be reliably used for determining the vitality of a tooth having been restored by a filling, crown or bridge.

DE19649689 discloses a method for determining the vitality of a tooth based on the ability to distinguish teeth with and without blood perfusion. The method involves irradiating the tooth in the vicinity of the pulp with non-ionising electromagnetic radiation. The intensity of the radiation transmitted from the tooth is measured as a function of the wavelength in a spectral range where the absorption coefficient of a blood containing substance has at least a maximum and a minimum. Two parameters are calculated from the measured intensities. For determining the vitality of a tooth, the method involves determining whether the pair of parameters lies within or outside a predetermined value range. A dental probe is used for determining the vitality of a tooth according to DE19649689, which is shown schematically in FIG. 13. The dental probe comprises a light emitter and a light receiver, wherein the light emitter emits light from an emitter surface adapted to be positioned on a hard dental surface of a tooth, and wherein the light receiver collects light incident on a receiver surface adapted to be positioned on a hard dental surface of the tooth so that the optical path of the light emitted from the light emitter passes at least through a portion of the pulp chamber of the tooth.

Although the concept of DE19649689 is useful for determining the vitality of a tooth, the variation of natural dental structures, the complex shape of the various coronary teeth and the complexity of measured intensities prevented high sensitivity and specificity. In particular, the probe body is large as compared to a tooth and cannot be reliably used for determining the vitality of a tooth having been restored by a filling, crown or bridge. Therefore, and despite continuous efforts in the field, the concept as disclosed by DE19649689 did not allow the development of any useful clinical method for decades.

None of the prior art addresses the problem of determining the vitality of a restored tooth having a restoration extending close to or beyond the gum line. A tooth having been restored by a filling, crown or bridge whereby the pulp chamber available for transillumination.

SUMMARY OF THE INVENTION

It is the problem of the present invention to provide a dental probe for determining the vitality of a tooth with high sensitivity and specificity in an objective and non-invasive method for qualitatively and quantitatively determining the status of a tooth with high reproducibility, in particular a tooth having been restored by a filling, crown or bridge.

According to a first aspect, the present invention provides a dental probe for determining the vitality of a tooth, comprising
 (A) a light emitter and
 (B) a light receiver,
  wherein the light emitter emits light from an emitter surface adapted to be positioned on a hard dental surface of a tooth,
  wherein the light receiver collects light incident on a receiver surface adapted to be positioned on a hard dental surface of the tooth so that the optical path of the light emitted from the light emitter passes at least through a portion of the pulp chamber of the tooth,
  characterized in that the light receiver comprises
   (a) a light shielding spacer member adjacent to the optical path for establishing and maintaining a distance of at least 50 µm between the gum line and the optical path at the receiver surface, and in that the light emitter comprises
   (c) a light shielding spacer member adjacent to the optical path for establishing and maintaining a distance between the gum line and the optical path at the emitter surface, wherein the light shielding spacer member establishes and maintains a distance of at least 50 µm between the gum line and the optical path at the emitter surface,
  and in that
  an apical-coronal diameter of the light emitter surface and the light receiver surface is at most 1200 µm in the direction normal to the optical path.

According to a specific embodiment, the present invention provides a dental probe according to the first aspect, wherein the light emitter surface and/or the light receiver surface forms part of a member adapted to be removably attached to the dental probe.

According to a second aspect, the present invention provides a dental system comprising the dental probe according to the first aspect and a control unit.

According to a third aspect, the present invention provides a member for a dental probe according to the specific embodiment of the first aspect, which comprises the light emitter surface and/or the light receiver surface, which member is disposable and/or sterilizable.

The present invention is based on the recognition that the method according to DE19649689 lacks sufficient sensitivity and specificity in practice since the detected light reflects not only the transmission and scattering properties of the pulp chamber, but a large portion of the tooth and adjacent soft dental tissue. Moreover, in case of the examination of a tooth having been restored by a filling, crown or bridge, the device according to DE19649689 often does not fit between the restoration and bone/jaw so that the method according to DE19649689 is completely inadequate regarding sensitivity and specificity.

Moreover, the present invention is based on the recognition that the contribution of the pulp to the detected light in the method according to DE19649689 is low. The present invention is also based on the recognition that in clinical practice, the method according to DE19649689 cannot be adapted to teeth having been treated by restorative methods given the limited space available below a dental crown.

Furthermore, the present invention is based on the recognition that it is possible to provide specific mechanical measures which significantly improve the sensitivity and specificity of the method of DE19649689. In particular, although a reduction of the diameter of the receiver and emitter deteriorates the signal to noise ratio of the device, it is possible to improve the signal to noise ratio by reducing the influence of ambient light, any restoration, hard dental tissue and soft dental tissue other than the dental pulp by a specific dental probe. According to the present invention, the apical-coronal diameter of the light emitter surface and the light receiver surface is at most 1200 µm in the direction normal to the optical path so that the dental probe may be positioned on a limited space of the tooth below a dental crown, without covering or excessively approaching soft dental tissue. The dental probe has a light shielding spacer member adjacent to the optical path for establishing and maintaining a distance between the gum line and the optical path at the receiver surface. Additionally, the dental probe may have a pressing member for engaging the gingiva by applying pressure onto the gum when the receiver surface is positioned on the tooth, thereby providing an anaemic condition of the gingiva.

Monte Carlo computer simulation (FIG. 14) results show that the influence of the pulp on the transmission spectrum compared to the influence of the gingiva on the spectrum may be increased by using a specific light shielding spacer member on the emitter and the receiver surface in combination with a specific diameter of the emitter and receiver surface. Accordingly, the vitality of a tooth, in particular of a tooth previously having been restored by a filling, crown or bridge, may be determined with high sensitivity and specificity even in case of a residual volume of pulp in the tooth. The sensitivity and specificity provided by the dental probe of the present invention is similar to the cold test, but does not relay on the subjective response by the patient.

BRIEF DESCRIPTION OF THE DRAWINGS

The patent or application file contains at least one drawing executed in color. Copies of the patent or patent application publication with color drawing(s) will be provided by the Office upon request and payment of the necessary fee.

FIG. 3A shows a front view of the receiver surface 124 and spacer member 126. FIG. 3B shows a side view of the receiver surface 124 and spacer member 126 shown in FIG. 3A.

FIG. 4A shows a front view of the receiver surface 124 and spacer member 126. FIG. 4B shows a perspective view of the receiver surface 124 and spacer member 126 shown in FIG. 4A.

FIG. 5A shows a front view of the receiver surface 124 and spacer member 126. FIG. 5B shows a perspective view of the receiver surface 124 and spacer member 126 shown in FIG. 5A.

FIG. 6A shows a front view of the receiver surface 124 and spacer member 126. FIG. 6B shows a perspective view of the receiver surface 124 and spacer member 126 shown in FIG. 6A.

DETAILED DESCRIPTION OF THE INVENTION

Sensitivity denotes the ability of a test to detect disease in patients who actually have the disease. Therefore, the sensitivity of a pulp vitality test indicates the test's ability to identify non-vital teeth. Sensitivity is defined as the ratio of the number of persons with a positive test result who have the disease divided by the total number of persons with the disease who were tested.

Specificity, on the other hand, describes the ability of a test to detect the absence of disease. Therefore, specificity of a pulp vitality test indicates the test's ability to identify vital teeth. Specificity is defined as the ratio of the number of patients with a negative test result who do not have disease divided by the total number of tested patients without the disease.

The positive and negative predictive values (PPV and NPV respectively) are the proportions of positive and negative results in the vitality tests that are true positive and true negative results.

Figure 1:
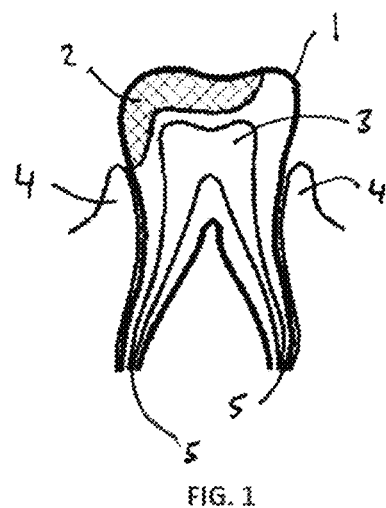
FIG. 1 shows a cross-sectional view of an adult jaw including a restored human tooth seated in the jaw bone and surrounded by gingiva.

FIG. 1 shows a cross-sectional view of an adult human tooth. The tooth 1 comprises enamel and dentin layers composed of hard, bone-like materials, wherein the principal inorganic component is hydroxyapatite. The enamel and possibly also the dentin layer may be replaced by a restoration 2 such as a filling, crown or bridge. The restoration 2 is not transparent to light of a wavelength of interest. Nerves and blood vessels enter and exit the pulp chamber 3 via the apical foramen 5. The pulp microvasculature comprises a dense network of capillaries, interconnect arterioles and venules which traverse the center of the pulp chamber 3. Blood perfusion of the dental pulp supplies oxygen, mineral salts, and other nutrients necessary to sustain the activity of odontoblasts and neural tissue associated with the dentin. The volume of the pulp chamber 3 relative to that of the entire tooth varies widely among individuals and also depends on the type of tooth and age of the patient. The tooth is surrounded by gingiva 4 in a collar like fashion. The gingiva 4 consists of the mucosal tissue that lies over the mandible and maxilla inside the mouth. The gingival connective tissue consists of a dense network of collagen fibers.

Collagen fibers function to provide firmness to the gingiva and to attach the gingiva to the underlying cementum and alveolar bone. The connective tissue of the gingiva is rich in blood. The blood circulating in the gingiva may interact with light. However, light does not contain information on the vitality of the pulp after an interaction with gingival blood. Rather, the detection of such light by the dental probe deteriorates the signal to noise ratio in the wavelength range used for the determination of the vitality of a tooth according to the present invention. Specifically, scattering of light from the light emitter of the dental probe of the present invention may increase the contribution of light scattered by gingival blood, which is detected by the receiver of the dental probe of the present invention. Moreover, scattering of ambient light may also increase the contribution of light scattered by gingival blood, which is detected by the receiver of the dental probe of the present invention. Since any light which has not previously interacted with the pulp deteriorates the signal to noise ratio, any light which has not previously interacted with the pulp must be avoided or prevented from reaching the light receiver.

The Dental Probe

The present invention provides a dental probe for determining the vitality of a tooth, in particular a tooth previously having been restored by a filling, crown or bridge. The dental probe is adapted to be used in the mouth of the patient. Specifically, the dental probe is adapted to be positioned consecutively on every tooth in the buccal/oral cavity. Given the orientation of the teeth in each of the four dental quadrants, the design of the dental probe, in particular the design of the emitter surface and the receiving surface preferably has symmetry properties. According to a first embodiment, a mirror plane is present between the emitter surface and the receiving surface. According to a further embodiment, a first mirror plane is present between the emitter surface and the receiving surface and a second mirror plane perpendicular to the first mirror plane is furthermore present, whereby the emitter surface and the receiving surface have two-fold symmetry.

Moreover, the dental probe is adapted to be sterile when used on a patient. For this purpose, notably the portions of the dental probe which are inserted into the buccal/oral cavity, may be used in combination with one or more transparent sterile disposable sheaths covering the portions of the dental probe. Alternatively, portions of the dental probe which are inserted into the buccal/oral cavity may be detachable and disposable. According to a particular aspect of the present invention, a disposable and/or sterilizable member for the dental probe is provided which comprises the light emitter surface or the light receiver surface.

Moreover, according to a preferred embodiment, the dental probe comprises a sensor for determining the distance between the emitting surface and the receiving surface when the dental probe is positioned on a tooth, whereby the width of the tooth under consideration may be determined and taken into account when determining the vitality of the tooth.

Advantageously, the dental probe is adapted to be handled single-handedly by the dental practitioner. For this purpose, the dental probe is preferably a cordless device. Preferably, the dental probe is powered by a battery. According to a preferred embodiment, the dental probe according is a cordless, handheld device. Any data exchange between the dental probe and a control unit is preferably provided by a wireless connection. The wireless connection may be one directional or bidirectional.

According to an alternative embodiment, the dental probe may be connected to a docking station or interface unit by a cable. The docking station or interface unit may comprise a display for displaying of the diagnostic results acquired by the dental probe.

The Light Emitter

The dental probe of the present invention comprises a light emitter. The light emitter comprises an emitter surface adapted to be positioned on a hard dental surface of a tooth. The emitter surface emits light. The emitter surface is transparent to light in the range of the spectrum of interest. The emitter surface may be the surface of a light source such as an LED.

Alternatively, the emitter surface forms part of an optical light guide. According to a preferred embodiment, the light emitter comprises an emitter light guide having a proximal end and a distal end, whereby the emitter light guide collects light at a proximal end and emits light at the distal end. More preferably, the distal end being integrally formed with the spacer member and/or the pressing member.

The emitter light guide may be made of a glass, quartz or plastic fiber optic rod extending from the light source to the emitter surface. Preferably, the light guides are made of polymeric resin optical fibers or glass fibers.

Generally, the light guide will be 3 to 20 cm long with a tip at the distal end thereof. The tip may have any desired shape preferably conforming to the surface geometry of a tooth being treated. Alternatively, a prism may be used to change the direction of the light in the direction of the emitter surface. By providing the emitter surface at the tip to conform to the geometry of the tooth surface, little radiant energy will be lost and adjacent soft and hard tissue surfaces will not be heated or damaged.

The light emitter further comprises a light radiating unit having a light source capable of emitting light. The light radiating unit is capable of selectively or simultaneously radiating light of a single wavelength or light having a wavelength spectrum.

The light source may include a light-emitting device constructed from an LED or a semiconductor laser diode. The light source may also include a light-emitting device selected from among a halogen lamp, a xenon lamp, a sodium lamp, a metal halide lamp, a mercury lamp, and a blacklight lamp.

The light radiating unit may further include an optical filter for selecting light of a designated wavelength from the light emitted from the light source.

According to a preferred embodiment, the light radiating unit includes a plurality of light sources for emitting light in different wavelength, and is capable of radiating light in one wavelength region by switching between the plurality of light sources or is capable of variably adjusting the light emission level of at least one of the light sources.

According to a preferred embodiment, the light radiating unit includes a plurality of light sources for emitting light at different wavelengths, and selects the light to be emitted by sequentially switching between the plurality of light sources, thereby sequentially radiating the light at the different wavelengths in a time-division fashion.

The one or more light sources may be disposed adjacent, to the emitting surface of the dental probe or adjacent to the proximal end of an optical light guide extending to the emitting surface.

The one or more light sources may be provided in an adapter having a mounting member. Each light source may include a plurality of light-emitting devices, wherein the plurality of light-emitting devices are arranged side by side in an end face portion of the adapter. The adapter may be equipped with a power supply for driving the light source, wherein the power supply may be a primary cell or a secondary cell. The power supply for driving the light source may be provided separately from the adapter, and the power supply may be detachably mounted on the body of the instrument.

Preferably, the light emitter comprises one or more LEDs and/or halogen lamps, which provide a light spectrum of from 500 to 650 nm, preferably 500 to 1500 nm.

According to a preferred embodiment, the emitter comprises two or more LEDs for sequentially emitting light, whereby the wavelength spectrum of the each LED is different from the wavelength spectrum of any other LED.

The Light Receiver

The dental probe of the present invention comprises a light receiver. The light receiver comprises a receiver surface adapted to be positioned on a hard dental surface of a tooth. The receiver collects light incident on a receiver surface. The receiver surface is adapted to be positioned on a hard dental surface of the tooth so that the optical path of the light emitted from the light emitter passes at least through a portion of the pulp chamber of the tooth. Preferably, the light receiver comprises a photodiode. Alternatively, the light receiver may be a spectrometer.

According to a preferred embodiment, the light receiver comprises a receiver light guide having a proximal end and a distal end, whereby the receiver light guide collects light at the distal end and emits light at the proximal end. Preferably, the receiver light guide comprises the receiver surface. The receiver light guide may be made of a glass, quartz or plastic fiber optic rod extending from the light source to the emitter surface. Preferably, the light guides are made of polymeric resin optical fibers or glass fibers.

The Apical-Coronal Diameter

The present invention is characterized in that an apical-coronal diameter of the light emitter surface and the light receiver surface is at most 1200 μm in the direction normal to the optical path. Preferably, the apical-coronal diameter of the light emitter surface and the light receiver surface is at most 800 μm, more preferably at most 500 μm in the direction normal to the optical path. According to a preferred embodiment, the apical-coronal diameter in the direction normal to the optical path of the light emitter surface is different from the apical-coronal diameter of the light receiver in the dental probe according to the invention. In view of the signal to noise ratio, the apical-coronal diameter of the light emitter surface and the light receiver surface is at least 50 μm, more preferably at least 100 μm in the direction normal to the optical path. The apical-coronal diameter of the light emitter surface and the light receiver surface may be defined as follows. In case of a circular light emitter surface or a circular light receiver surface, the apical-coronal diameter is the diameter of the light emitter surface or the light receiver surface. In case of a non-circular light emitter surface or non-circular light receiver surface, the apical-coronal diameter is the length of a straight line segment that passes through the centre of the surface and whose endpoints lie on the circumference of the surface in apical-coronal direction when the light emitter surface or the light receiver surface is placed on the tooth.

The Light Shielding Spacer

The dental probe is characterized in that the light receiver comprises a light shielding spacer member adjacent to the optical path for establishing and maintaining a distance between the gum line and the optical path at the receiver surface. The light shielding spacer serves to shield the receiver from light which did not interact with pulp. Specifically, the light shielding spacer serves to shield the receiver from light scattered by the hard and soft dental tissue in the vicinity of the pulp, which light did not interact with pulp, and to shield the receiver from ambient light incident from the environment of the tooth. Moreover, the light shielding spacer serves to establish and maintain a distance between the light receiving surface and the dental gum line in order to avoid any radiation after interaction with the blood circulating in the gum. Any light which did not interact with the pulp deteriorates the signal to noise ratio of the measurement.

Moreover, the light emitter comprises a light shielding spacer member adjacent to the optical path for establishing and maintaining a distance between the gum line and the optical path at the emitting surface. The light shielding spacer serves to shield the hard and soft dental tissue other than the pulp in the vicinity of the pulp. Moreover, the light shielding spacer serves to establish and maintain a distance between the light emitting surface and the dental gum line in order to avoid interaction of light with the blood circulating in the gum. Any light which did not interact with the pulp deteriorates the signal to noise ratio of the measurement.

It is preferred that the light shielding spacer member establishes and maintains a distance between the gum line and the optical path at the emitter and/or receiver surface of at least 50 μm. More preferably, the light shielding spacer member establishes and maintains a distance between the gum line and the optical path at the emitter and/or receiver surface of at least 100 μm, in particular at least 200 μm. The light shielding spacer member establishes and maintains a distance between the gum line and the optical path at the emitter and/or receiver surface of at most 1000 μm, in particular at most 800 μm. Preferably, the receiver surface and/or the emitter surface and the distal surface of the light shielding spacer member are in the same plane, respectively.

The light shielding property of the light shielding spacer member may be provided by using an intransparent material in the range of the wavelength spectrum which is of interest so that light which has passed through portions of the gingiva cannot reach the receiver surface. A preferred material for the light shielding spacer member is selected from a resin or a metal. Preferably, the material is a resin which may be a composite resin containing a filler.

The Pressing Member

The dental probe may be characterized in that the light receiver comprises a pressing member for engaging the gingiva by applying pressure onto the gum when the receiver surface is positioned on the tooth, thereby providing an anaemic condition of the gingvia. For this purpose, the receiver surface and/or the emitter surface and the distal surface of the pressing member are in different planes, whereby the distal surface of the pressing member is retracted in the proximal direction relative to the receiver surface and/or the emitter surface, respectively. The distance between the planes is selected so that a portion of the gingiva may be pressed while the receiving surface is placed on the hard dental structure of the tooth. Preferably, the distance is in the range of 300 μm to 5000 μm.

According to a preferred embodiment, the light emitter also comprises a light shielding spacer member adjacent to the optical path for establishing and maintaining a distance between the gum line and the optical path at the emitter surface. Alternatively or additionally the light emitter also comprises a pressing member for engaging the gingiva by applying pressure onto the gum when the emitter surface is positioned on the tooth, thereby providing an anaemic condition of the gingiva.

In general, the light shielding spacer member and the pressing member may be integral parts of a combination member.

According to a specific embodiment, the dental probe further comprises a second light receiver for detecting scattered light.

According to a preferred embodiment, the light emitter surface and/or the light receiver surface forms part of a member adapted to be removably attached to the dental probe.

The present invention also provides a dental system comprising the dental probe according to the invention and a control unit.

The dental system may further comprise a sensor for determining the position of the tooth to be measured, whereby the dental system stores the measured vitality value and position for each measured tooth.

According to a preferred embodiment, the dental system according to the invention comprises a wireless connection between the dental probe and a practice management system for transmitting or exchanging data between the dental probe and the practice management system.

The present invention also relates to a member for a dental probe which comprises the light emitter surface or the light receiver surface, which member is disposable and/or sterilizable.

The dental probe of the present invention may be used as an objective method for assessing the state of the pulp by evaluating the blood flow in the dental cavity through optical methods such as laser Doppler flowmetry, photoplethysmography, spectrophotometry and pulse oximetry. Preferably, the dental probe of the present invention is used with pulse oximetry.

According to a preferred embodiment, the portions of the dental probe according to the present invention which are inserted into the oral cavity may be used in combination with one or more transparent sterile disposable sheaths covering the portions of the dental probe. The sheath protects portions of the dental probe and avoids contamination of the patient. In an embodiment, a sheath may have matching oil for adjusting the refractive index and filling the space between the sheath and the dental probe according to the present invention. The refractive index of the matching oil may be equal to or approximately equal to the refractive index of the light emitting or receiving surface.

The present invention will now be further explained based on the enclosed figures.

Figure 2:
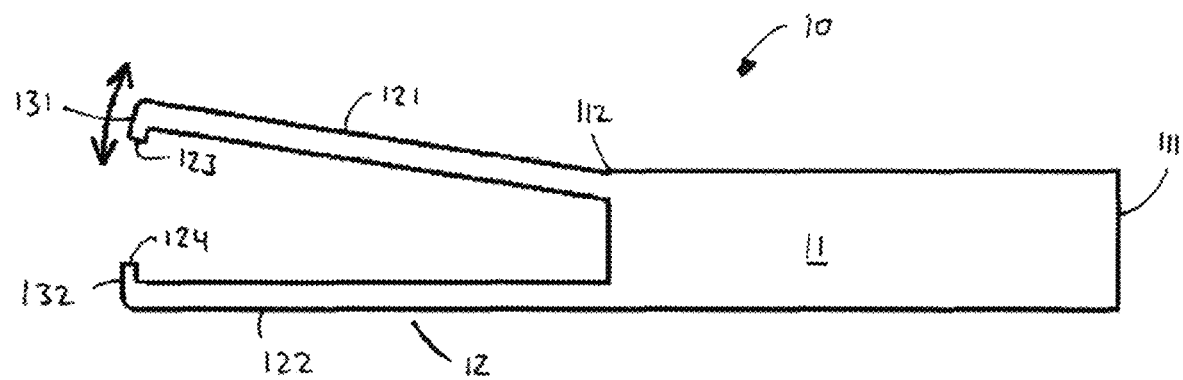
FIG. 2 shows a schematic top view of a dental probe (10) according to the present invention.

FIG. 2 shows a schematic top view of a dental probe (10) according to the present invention. The dental probe comprises a handle portion 11 and a plier portion 12. The handle portion 11 has a proximal end 111 and a distal end 112. The handle portion 11 comprises a housing. The housing may hold one or more light sources, one or more photodiodes, a spectrometer, optical filter, a power supply, control circuitry, and a user interface. The housing may also contain an antenna for wireless communication. Furthermore, the housing may be adapted to measure the distance between the emitter surface 124 and the receiver surface 123 when the dental probe is positioned on a tooth. The distance corresponds to the tooth width and may be used for further improvement and interpretation of the diagnostic result.

Preferably, the housing is formed of a thermally conductive material, a thermally conductive printed circuit board shaped to fit within the housing and positioned in direct thermal contact with the housing, and a plurality of light sources such as light emitting diodes (LED) coupled to the circuit board. The direct thermal contact between the printed circuit board and the housing facilitates dissipation of heat generated by the LED light sources. The thermally conductive printed circuit board can comprise a circuit layer, a dielectric layer comprising a dielectric material, and a thermally conductive substrate layer comprising aluminum or copper.

The handle portion 11 may further be provided with control functions and/or display functions. For example, the handle portion 11 may include an activation button (not shown). A battery status indicator may be preferably provided. Furthermore, protection against battery exhaustion may be provided by a warning signal at a critical battery level.

Moreover, the handle portion may further comprise a multifunction button and/or a bluetooth button. Furthermore, art automated wake-up function may be implemented by using an accelerometer.

Advantageously, the handle portion 11 comprises a display for displaying diagnostic results. The display may be provided at any surface of the handle portion.

A measurement trigger may be implemented in the handle portion which triggers a measurement as soon as the dental probe is properly positioned on a tooth. The trigger may be defined based on a non-saturated and stable state of the receiver and optionally the accelerometer which indicates stable positioning of the dental probe of the present invention on a tooth.

At the distal end of the handle, the plier portion 12 is provided. The plier portion is used for contacting a single tooth. The plier portion comprises a first leg 121 and a second leg 122. At least one leg 121 may be swivelled about an axis of rotation or bent toward the opposing leg. Preferably, a first leg is stationary and a second leg may be swivelled or bent. Preferably, the first leg is the receiver leg.

At the distal end of the emitter leg, the emitter surface 123 is provided. At the distal end of the receiver leg, the receiver surface 124 is provided. Legs 121 and 122 are adapted to grasp any tooth in the buccal oral cavity of a patient so that the emitter surface 123 and the receiver surface 124 are positioned on opposite sides of the tooth. For this purpose, the emitter surface 123 and the receiver surface 124 are adapted to be positioned on a hard dental surface of a tooth. The emitter surface 123 and the receiver surface 124 are provided on projections 131, 132 of the corresponding legs 121, 122, respectively. The projections 131, 132 project in opposite directions toward the surface of a tooth, when the tooth is introduced between legs 121, 122.

The surfaces 123, 124 may be coated by a coating facilitating the transmission of light through the interface of the between the emitter surface 123 or receiver surface 124 and the surface of the tooth. When the emitter surface 123 is placed on the labial side of the tooth, then the receiver surface 124 is placed on the lingual side of the tooth. Alternatively, when the emitter surface 123 is placed on the lingual side of the tooth, then the receiver surface 124 is placed on the labial side of the tooth. The dental practitioner will use the dental probe of the present invention for testing the vitality of the teeth of a patient one tooth at a time.

The emitter surface 123 and the receiver surface 124 define an optical path. The positioning of the emitter surface 123 and the receiver surface 124 is such that the optical path traverses at least a portion of the pulp chamber of the tooth. On the other hand, the emitter surface 123 and the receiver surface 124 are adapted so that the positioning below a restoration such as a dental crown, and at a defined distance above the gum line is possible.

According to a preferred embodiment, the emitter surface 123 and the receiver surface 124. The emitter surface 123 and the receiver surface 124 define a labial-lingual distance corresponding to the length of the optical path. The apical-coronal diameter of the light emitter surface and the light receiver surface is at most 1200 µm in the direction normal to the optical path.

Figure 3A:
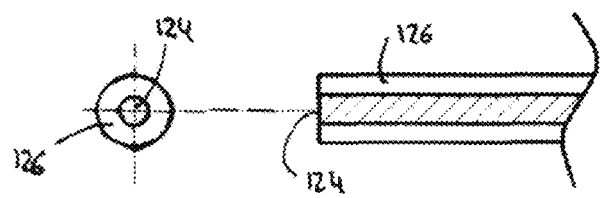
FIGS. 3A and 3B shows a partial view of a dental probe according to a first embodiment of the present invention, which includes a light receiving surface and a light shielding spacer member adjacent to the optical path for establishing and maintaining a distance between the gum line and the optical path at the receiver surface. More specifically.
Figure 3B:
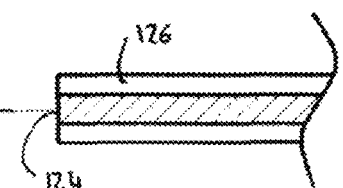

FIGS. 3A and 3B shows a partial view of a dental probe according to a first embodiment of the present invention, which includes a light receiving surface 124 and a light shielding spacer member 126 adjacent to the optical path for establishing and maintaining a distance between the gum line and the optical path at the receiver surface 124.

FIG. 3A shows a front view of the receiver surface 124 and spacer member 126. The diameter of the circular receiver surface 124 is at most 1200 µm. The receiver surface is at the distal end of a light guide. Accordingly, the receiver surface may be easily placed on the surface of a tooth. In order to keep a defined distance between the gum line and the receiver surface and in order to shield the receiver surface from scatter light from the gingiva, a spacer member 126 is provided.

FIG. 3B shows a side view of the receiver surface 124 and spacer member 126 shown in FIG. 3A. As shown, the front surface of the spacer member and the receiver surface are provided in the same plane. Accordingly, the light shielding effect and the distance-keeping function of the spacer member 126 may be optimized.

According to the present invention a light guide having a small diameter may be introduced into a metal tube providing mechanical stability and at the same time serving as a spacer member 126. Accordingly, the diameter of the light guide may be selected to be small, e.g from 50 to 600 µm.

Alternatively, a light guide having a larger diameter may be coated by a resilient material conforming to the outer shape of the tooth. The resilient material may be preferably silicone.

Figures 4A, 4B:
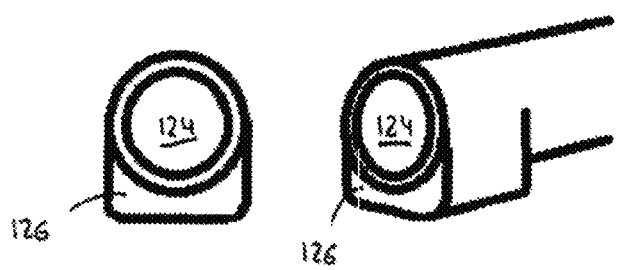
FIGS. 4A and 4B shows a partial view of a dental probe according to a second embodiment of the present invention, which includes a light receiving surface and a light shielding spacer member adjacent to the optical path for establishing and maintaining a distance between the gum line and the optical path at the receiver surface. The light shielding spacer is provided only partially around the circumference of the light receiving surface.

FIGS. 4A and 4B shows a partial view of a dental probe according to a second embodiment of the present invention, which includes a light receiving surface 124 and a light shielding spacer member 126 adjacent to the optical path for establishing and maintaining a distance between the gum line and the optical path at the receiver surface 124.

FIG. 4A shows a front view of the receiver surface 124 and spacer member 126. The diameter of the circular receiver surface 124 is at most 1200 µm. The receiver surface is at the distal end of a light guide. Accordingly, the receiver surface may be easily placed on the surface of a tooth. In order to keep a defined distance between the gum line and the receiver surface and in order to shield the receiver surface from scatter light from the gingiva, a spacer member 126 is provided.

FIG. 4B shows a perspective view of the receiver surface 124 and spacer member 126 shown in FIG. 4A. As shown, the front surface of the spacer member and the receiver surface are provided in the same plane. Accordingly, the light shielding effect and the distance-keeping function of the spacer member 126 may be optimized.

Figures 5A, 5B:
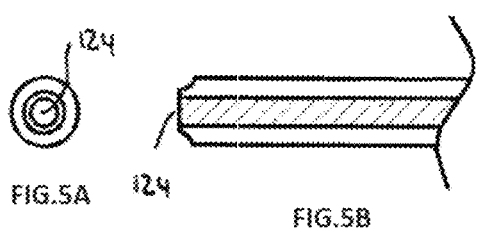
FIGS. 5A and 5B shows a partial view of a dental probe according to a third embodiment of the present invention, which includes a light receiving surface and a pressing member for engaging the gingiva by applying pressure onto the gum when the receiver surface is positioned on the tooth, thereby providing an anaemic condition of the gingvia. The pressing member is integral with a light shielding spacer member adjacent to the optical path for establishing and maintaining a distance between the gum line and the optical path at the receiver surface.

FIGS. 5A and 5B shows a partial view of a dental probe according to a third embodiment of the present invention, which includes a light receiving surface and a pressing member for engaging the gingiva by applying pressure onto the gum when the receiver surface is positioned on the tooth, thereby providing an anaemic condition of the gingvia. The pressing member and the light shielding spacer member are integral parts of a combination member adjacent to the optical path for establishing and maintaining a distance between the gum line and the optical path at the receiver surface.

FIG. 5A shows a front view of the receiver surface 124 and spacer member 126. The diameter of the circular receiver surface 124 is at most 1200 µm. The receiver surface is at the distal end of a light guide. Accordingly, the receiver surface may be easily placed on the surface of a tooth. In order to keep a defined distance between the gum line and the receiver surface and in order to shield the receiver surface from scatter light from the gingiva, a spacer member 126 is provided.

FIG. 5B shows a perspective view of the receiver surface 124 and spacer member 126 shown in FIG. 5A. As shown, the front surface of the spacer member and the receiver surface are provided in the same plane. Accordingly, the light shielding effect and the distance-keeping function of the spacer member 126 may be optimized. Moreover, a pressing member is provided for engaging the gingiva by applying pressure onto the gum when the receiver surface is positioned on the tooth, thereby providing an anaemic condition of the gingvia.

Figures 6A, 6B:
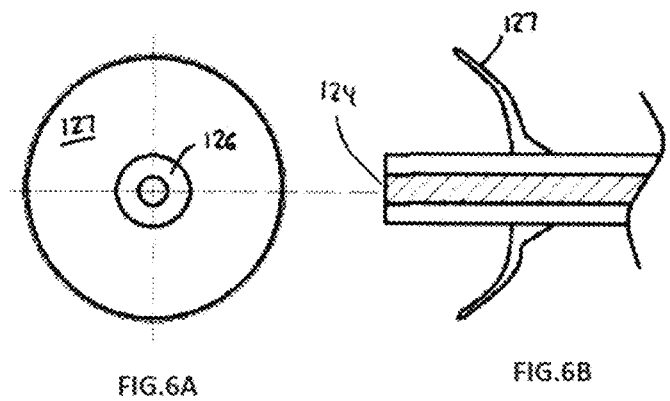
FIGS. 6A and 6B shows a partial view of a dental probe according to a fourth embodiment of the present invention, which includes a light receiving surface and a light shielding spacer member adjacent to the optical path for establishing and maintaining a distance between the gum line and the optical path at the receiver surface. Additionally, a shielding member is provided for shielding the receiving surface from ambient light.

FIGS. 6A and 6B shows a partial view of a dental probe according to a fourth embodiment of the present invention, which includes a light receiving surface 124 and a light shielding spacer member 126 adjacent to the optical path for establishing and maintaining a distance between the gum line and the optical path at the receiver surface. Additionally, an additional shielding member 127 is provided for shielding the receiving surface 124 from ambient light.

FIG. 6A shows a front view of the receiver surface 124 and spacer member 126. The diameter of the circular receiver surface 124 is at most 1200 µm. In order to keep a defined distance between the gum line and the receiver surface and in order to shield the receiver surface from scatter light from the gingiva, a spacer member 126 is provided.

FIG. 6B shows a perspective view of the receiver surface 124 and spacer member 126 shown in FIG. 6A. As shown, the front surface of the spacer member and the receiver surface are provided in the same plane. Accordingly, the light shielding effect and the distance-keeping function of the spacer member 126 may be optimized.

Figure 7:
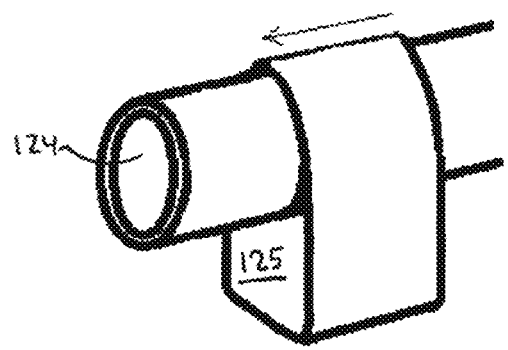
FIG. 7 shows a partial view of a dental probe according to a fifth embodiment of the present invention, which includes a light receiving surface and a light shielding spacer member adjacent to the optical path for establishing and maintaining a distance between the gum line and the optical path at the receiver surface, and additionally a pressing member for engaging the gingiva by applying pressure onto the gum when the receiver surface is positioned on the tooth, thereby providing an anaemic condition of the gingvia.

FIG. 7 shows a partial view of a dental probe according to a fifth embodiment of the present invention, which includes a light receiving surface and a pressing member 125 for engaging the gingiva by applying pressure onto the gum when the receiver surface is positioned on the tooth, thereby providing an anaemic condition of the gingvia. A spacer member 126 is also provided.

Figure 8:
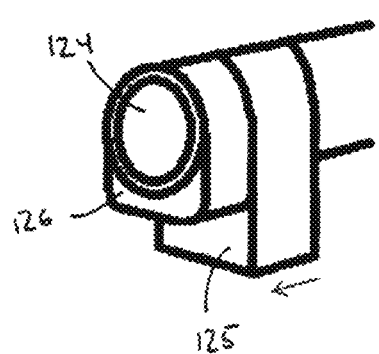
FIG. 8 shows a partial view of a dental probe according to a sixth embodiment of the present invention, which includes a light receiving surface and a light shielding spacer member adjacent to the optical path for establishing and maintaining a distance between the gum line and the optical path at the receiver surface, and additionally a pressing member for engaging the gingiva by applying pressure onto the gum when the receiver surface is positioned on the tooth, thereby providing an anaemic condition of the gingvia.

FIG. 8 shows a partial perspective view of a dental probe according to a sixth embodiment of the present invention, which includes a light receiving surface 124 and a light shielding spacer member 126 adjacent to the optical path for establishing and maintaining a distance between the gum line and the optical path at the receiver surface, and additionally a pressing member 125 for engaging the gingiva by applying pressure onto the gum when the receiver surface is positioned on the tooth, thereby providing an anaemic condition of the gingvia.

Figure 9:
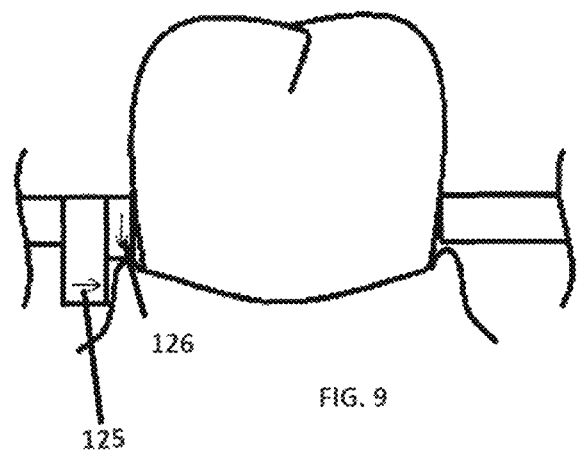
FIG. 9 shows a partial view of a dental probe according to the sixth embodiment of the present invention when applied to a tooth.

FIG. 9 shows a partial view of a dental probe according to the sixth embodiment of the present invention when applied to a tooth. As shown, the light shielding spacer member 126 adjacent to the optical path establishes and maintains a distance between the gum line and the optical path at the receiver surface. Moreover, since the receiver surface is positioned on the tooth, the pressing member 125 engages the gingiva by applying pressure onto the gum, thereby providing an anaemic condition of the gingvia.

Figure 10:
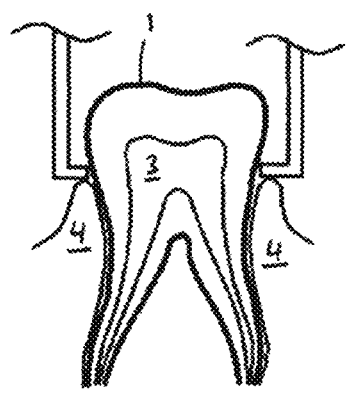
FIG. 10 shows a further partial view of a dental probe according to the first embodiment of the present invention when applied to a tooth.

FIG. 10 shows a further partial view of a dental probe according to the first embodiment of the present invention when applied to a tooth.

Figure 11A:
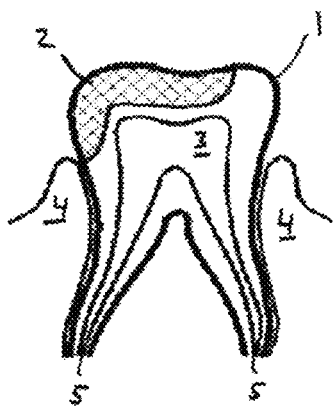
FIG. 11A shows the cross-sectional view of an adult jaw including a restored human tooth seated in the jaw bone and surrounded by gingiva similar to FIG. 1.
Figure 11B:
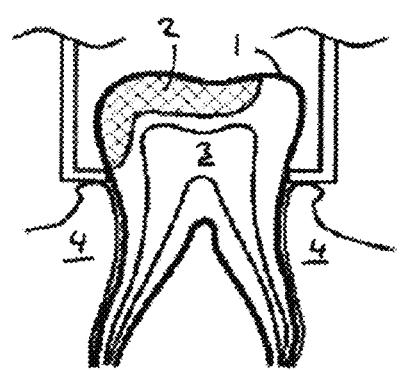
FIG. 11B shows a partial view of a dental probe according to the first embodiment of the present invention when applied to the tooth shown in FIG. 11A.

FIG. 11A shows the cross-sectional view of an adult jaw including a restored human tooth seated in the jaw bone and surrounded by gingiva similar to FIG. 1. FIG. 11B shows a partial view of a dental probe according to the first embodiment of the present invention when applied to the tooth shown in FIG. 11A.

The dental probe according to the present invention is positioned below the restoration and at a distance from the gingiva although the gingiva is displaced by the action of the dental probe according to the present invention. Given that the apical-coronal diameter of the light emitter surface and the light receiver surface is at most 1200 µm in the direction normal to the optical path, the restoration does not deteriorate the determination of the vitality of the tooth. Moreover, given the distance between the receiver surface and the gingiva due to the light shielding spacer member, the influence of light which did not interact with the pulp is low.

Figure 12:
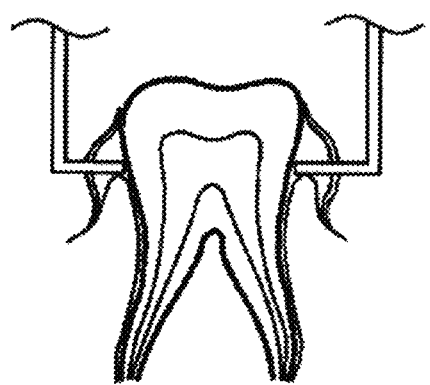
FIG. 12 shows a partial view of a dental probe according to the fourth embodiment of the present invention when applied to a tooth previously having been restored.
Figure 13:
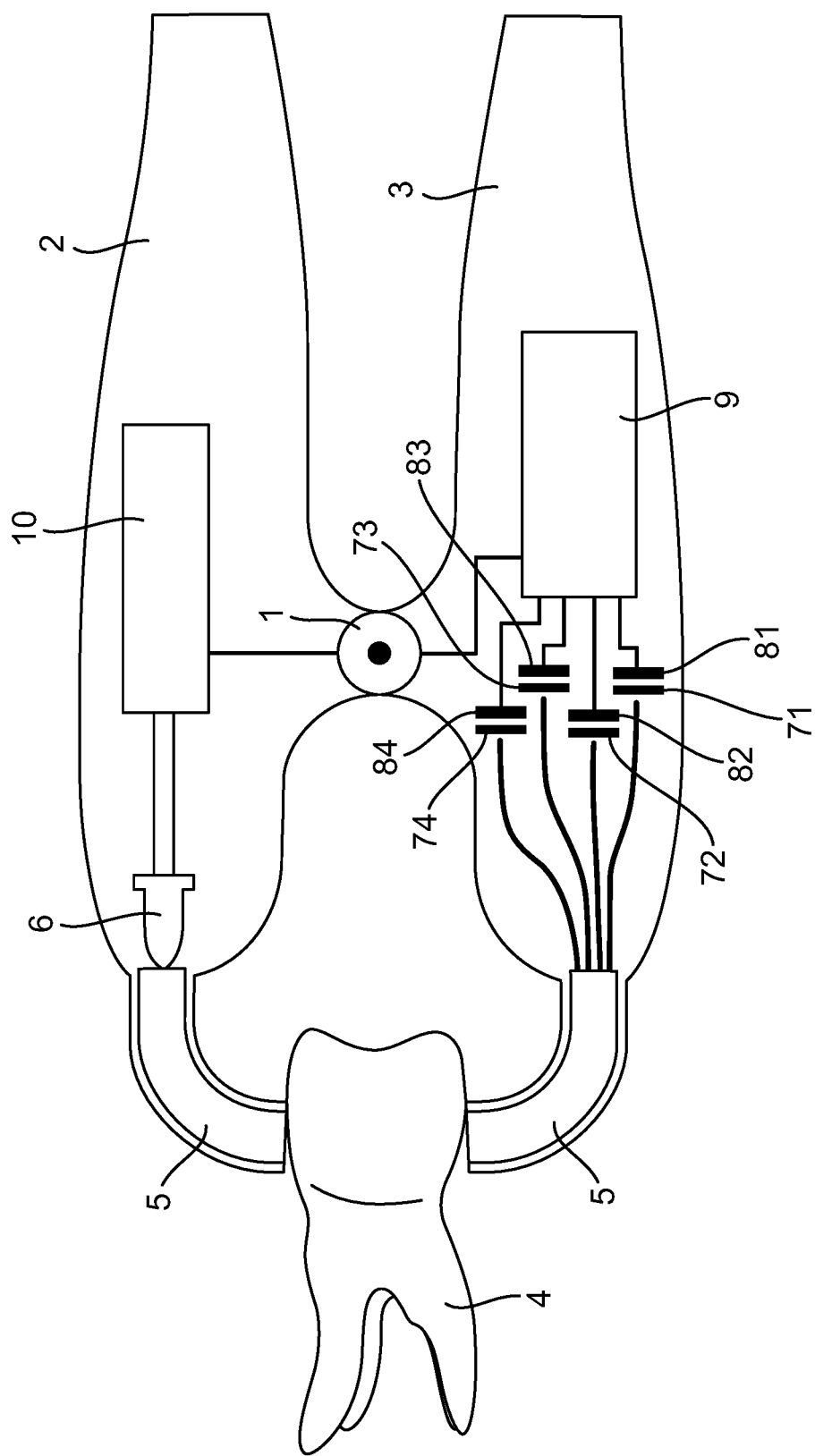
FIG. 13 shows schematically a dental probe for determining the vitality of a tooth of the prior art according to DE19649689.

FIG. 12 shows a partial view of a dental probe according to the fourth embodiment of the present invention when applied to a tooth previously having been restored. The receiver surface and the emitter surface are positioned on the tooth, the additional shielding member engages the gingiva and shields the receiver surface from ambient light. Moreover, the additional shielding member may also server to provide an anaemic condition of the gingvia.

Pulse oximetry is based on the interaction of light and matter according to the Beer-Lambert equation linking the intensity attenuation with properties of the medium and light wavelength. Accordingly, attenuation depends on the wavelength of the incidence light whereby the fraction of transmitted light can then be expressed by an exponential term that depends on the wavelength of the incidence light and on the travelling length. Given that oxygen concentration in blood has a particular impact on light attenuation, it is possible to determine the percentage of oxygen saturation in blood as long as different wavelengths are used to determine the same number of transmitted light fractions Pulse oximetry commonly use wavelengths of 660 nm (red) and 940 nm (infrared—IR).

The method may also take advantage of blood pulsation during cardiac cycle. In systole, arteries contain more blood than in diastole. In turn, in diastole, arteries have a larger amount of absorbent substances, such as haemoglobin and also a larger optical distance. Accordingly, light attenuation increases during systole. This dynamic portion of total absorption allows to discriminate absorption due to static components (venous blood, a constant amount of arterial blood and other invariants such as skin pigmentation) and absorption due to the pulsatile component (blood flow in the arteries).

These components are also denominated as DC and AC components of the total absorption, respectively. By arranging measures of DC and AC components from the two wavelengths it is possible to have an estimate of oxygen saturation.

Optical density variations resulting from the periodic fluctuations in the flow of blood to the tooth over the cardiac cycle can be sensed using a transmission spectrophotometer. Light emitted from a source placed on the surface of a tooth undergoes scattering and absorption by the enamel and dentin layers. Some of the photons that enter the soft tissue in the pulp chamber are scattered and absorbed by red blood cells, and a fraction of the forward-scattered light may be captured by the detector. Small changes in the absorption and scattering coefficients of the pulp tissue caused by a transient redistribution of red blood cells within the pulp cavity during systole results in a reduction in the light flux captured by the detector. In this manner, pulsatile blood flow in the tooth is detectable as a transient decrease in the received light intensity (i.e. increase in optical density) synchronous with contractions of the heart.

Sensitivity to the flow-related intensity variations, expressed in terms of the ratio of the amplitudes of the pulsatile ('AC') and non-varying ('DC') components of the photoamplifier output signal, depends on the wavelength at which the intensity is measured. Sensitivity is greatest at wavelengths in the green-orange wavelength band (540-600 nm) where the sum of the scattering and absorption coefficients of oxygenated whole blood is greatest.

Figure 14:
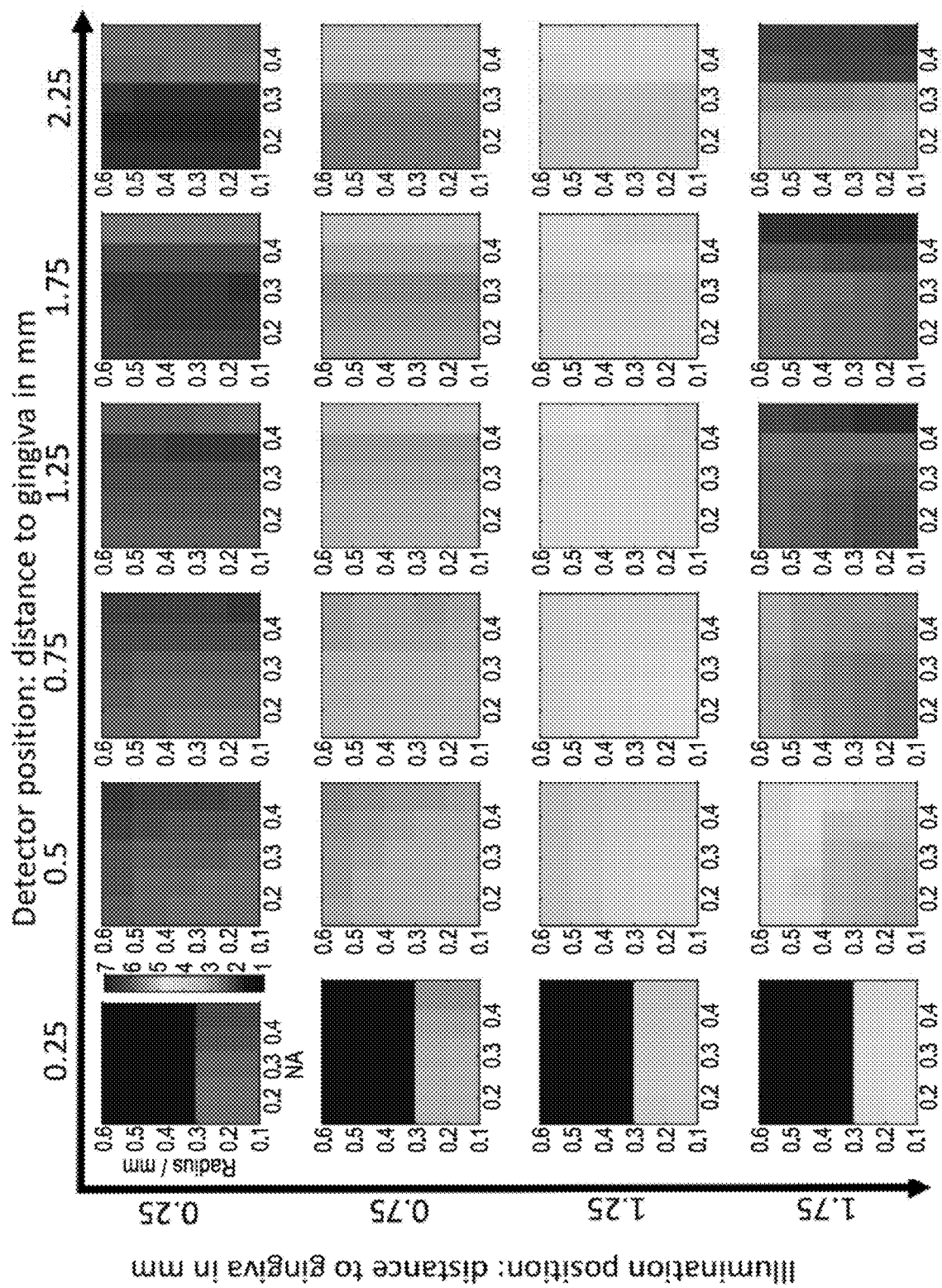
FIG. 14 shows the results of a Monte Carlo computer simulation of mean alpha for the spectral range of 500 nm to 640 nm, depending on different NA, radii, detector positions and illumination positions.

The influence of the illumination fiber position, detection fiber position, radius of the detection fiber and NA of the detection fiber was investigated by Monte Carlo computer simulations (FIG. 14). For this purpose, photons were simulated as particles propagating in a media according to physical laws, including Beer-Lambert law and Fresnel equations. A statistical approach is used to calculate the light propagation in turbid media by simulating many photons. The medium was represented by the surfaces of an object whereby the space between the surfaces is filled with tetrahedrons. A material with appropriate optical properties is assigned to each tetrahedron. Accordingly, a portion of the oral space including hard and soft dental tissue may be defined by the medium. In particular, the tooth geometry was adapted such that a root canal treated tooth can be simulated by addressing additional tetrahedrons to the mesh which represent the filling material. Anisotropic light propagation via dentine tubuli was taken into account by the model.

Illumination and detection was modelled by using models of optical fiber with defined NA, radius and position relative to the gingiva. The influence of the pulp on the spectrum compared to the influence of the gingiva on the spectrum was investigated. In order to compare the influence of the pulp and the gingiva a factor Alpha was used which is defined as Alpha=(Influence of the pulp)/(Influence of the gingiva).

For example at a certain wavelength $\lambda 1$, Alpha($\lambda 1$)=5 means that the influence of the pulp on the spectrum is 5 times higher than the influence of the gingiva on the spectrum for the wavelength $\lambda 1$.

In general, one can better distinguish the signal of the pulp from the signal of the gingiva for a higher factor Alpha. The illumination and detection for simulations is realized by a fiber placed 0.5 mm above the gingiva. The fibers are in contact with the tooth. Both fibers have a diameter of 500 µm and a NA of 0.22. The illumination fiber is placed on the front of the tooth and the detection fiber is placed on the back. The resulting transmission spectra are detected at the detection fiber on the back side of the tooth for the different materials inside the pulp.

Since the Monte Carlo method leads to absolute values for the power fractions (percentage of the incident light), the correct power fractions can be calculated for the different transmission spectra. The power fraction of the transmitted spectra are always stated in percentage of the power of the incident light for each wavelength.

The calculation of the factor Alpha is carried out as follows.

A "final spectrum" is calculated as a spectrum one would normally detect.

A "no absorption spectrum" is calculated as a spectrum if the dentin and enamel would have their normal absorption but the pulp and gingiva have 0 absorption.

An area (a) in the spectrum is identified corresponding to the influence of the pulp on the "no absorption spectrum" by setting the absorption in the pulp to its normal value while keeping the absorption in the gingiva at 0.

An area (b) is identified corresponding the influence of the gingiva on the "no absorption spectrum" by setting the absorption in the gingiva to its normal value and keeping the absorption in the pulp at 0.

Alpha is then determined as the ratio of the area (a) over the area (b) for each wavelength.

The influence of the following four components on the factor Alpha was investigated. The four components are:

1. Position of the Illumination Fiber

The distance of the illumination fiber to the gingiva is varied. Four different distances of the fiber center to the gingiva have been analyzed: 0.25 mm (the illumination fiber edge is almost in contact with the gingiva), 0.75 mm, 1.25 mm and 1.75 mm. The radius and NA of the illumination fiber is kept constant (NA=0.22, radius=0.25 mm).

2. Position of the Detection Fiber

For each illumination position six different detector positions have been analyzed. Therefore the distance of the detection fiber center to the gingiva is varied: 0.25 mm (the detection fiber edge is almost in contact with the gingiva), 0.5 mm, 0.75 mm, 1.25 mm, 1.75 mm and 2.25 mm.

3. Radius of the Detection Fiber

For each detector position 5 different radii of the detection fiber have been analyzed: 0.15 mm, 0.25 mm, 0.35 mm, 0.45 mm and 0.55 mm. For the detector positioned closest to the gingiva only the smallest two radii have been analyzed since the detection fiber would have touched the gingiva for bigger radii.

4. Numerical Aperture (NA) of the Detection Fiber.

For each detector position and each radius 5 different NAs of the detection fiber have been analyzed: 0.17, 0.24, 0.31, 0.38 and 0.45.

For each combination of the four components the factor alpha was calculated over the whole spectrum from 350 nm to 1000 nm. For better comparison a mean Alpha was calculated for two different wavelength ranges. In FIG. 14 the mean Alpha for the wavelength range of 500 nm to 640 nm is shown for each combination of detection fiber, illumination fiber, radius and NA. Similar results are obtained for the wavelength region from 350 nm to 500 nm and 640 to 1000 nm (not shown).

For both ranges, the results are similar:

Alpha increases with increasing distance of the illumination fiber to the gingiva For small distances of the detection fiber to the gingiva (0.25 mm, 0.5 mm and 0.75 mm) one gets the highest Alpha for a small radius and a small NA.

For large distances of the detection fiber to the gingiva (1.75 mm and 2.25 mm) one gets the highest Alpha for a small radius but a large NA.

Conclusion:

The simulation results show that the influence of the pulp on the transmission spectrum compared to the influence of the gingiva on the spectrum is increasing for larger distances of the illumination fiber to the gingiva. For the detection fiber a small radius leads almost in all cases to a higher Alpha. The NA of the detection fiber should be chosen small if the detection fiber is placed close the gingiva and should be chosen large if the detection fiber is placed at a rather large distance to the gingiva.

According to a preferred embodiment, an apical-coronal diameter of the light emitter surface and the light receiver surface is at most 300 μm in the direction normal to the optical path whereby the light shielding distance member provides a distance of up to 1 mm from the gingiva, whereby the light emitter and the light receiver have an NA of at most 0.3.

According to another preferred embodiment, an apical-coronal diameter of the light emitter surface of the light emitter and the light receiver surface of the light receiver is at most 300 μm in the direction normal to the optical path, whereby the light shielding distance member provides a distance of more than 1 mm from the gingiva and the light emitter and the light receiver have an NA of greater than 0.3.

Subsequently, the influence of different pulp sizes was investigated in order to evaluate the influence of different pulp sizes on the transmission spectra. Accordingly, the pulp of an incisor tooth model has been manipulated such that its volume is reduced to 25% and 6% of the original pulp volume. The transmission spectra for the two manipulated tooth models were calculated. For each tooth model two transmission spectra were calculated. For the first spectrum it has been assumed that the pulp is filled with oxygenated blood. For the second spectrum it has been assumed that the pulp is filled with deoxygenated blood. For the calculation of both spectra it has been assumed that the gingiva is filled with oxygenated blood.

It was found that it is possible to distinguish the two blood types for this tooth model. At the tooth models where the pulp was reduced to 6%, the transmission spectrum for the deoxygenated pulp case shows only a glimpse of the double peak at 560 nm.

The simulation results show that even for smaller (75% smaller) pulps one should be able to distinguish oxygenated blood from deoxygenated blood. Only for really small pulps (94% smaller) it is not that clear anymore.

The invention claimed is:

1. A dental probe for determining the vitality of a tooth, comprising
    a light emitter;
    a light receiver, and
    a pressing member for engaging a gingiva by applying pressure onto a gum when the receiver surface is positioned on the tooth, thereby providing an anaemic condition of the gingiva;
    wherein the light emitter emits light from an emitter surface adapted to be positioned on a hard dental surface of a tooth,
    wherein the light receiver collects light incident on a receiver surface adapted to be positioned on the hard dental surface of the tooth so that an optical path of the light emitted from the light emitter passes at least through a portion of a pulp chamber of the tooth,
    wherein the light receiver includes a first light shielding spacer member adjacent to the pressing member and extends along a direction of the optical path for establishing and maintaining a distance of 50 μm to 1000 μm between a gum line and the optical path at the receiver surface, and
    wherein the light emitter includes a second light shielding spacer member adjacent to the pressing member and extends along a direction of the optical path for establishing and maintaining a distance between the gum line and the optical path at the emitter surface, wherein the second light shielding spacer member establishes and maintains a distance of 50 μm to 1000 μm between the gum line and the optical path at the emitter surface, and wherein an apical-coronal diameter of the light emitter surface and the light receiver surface is at most 1200 μm in the direction normal to the optical path.

2. The dental probe according to claim 1, wherein the pressing member of the light emitter is configured to engage the gingiva by applying pressure onto the gum when the emitter surface is positioned on the tooth, thereby providing an anaemic condition of the gingiva.

3. The dental probe according to claim 1, wherein the light emitter includes at least one of one or more LEDs or a halogen lamp, which provide a light spectrum of from 500 to 1000 nm.

4. The dental probe according to claim 1, wherein the light receiver includes a photodiode, wherein the emitter includes two or more LEDs for sequentially emitting light, whereby the wavelength spectrum of each LED is different from the wavelength spectrum of any other LED, or wherein the light receiver includes a spectrometer.

5. The dental probe according to claim 1, wherein the light emitter includes a light guide having a proximal end and a distal end, whereby the emitter light guide collects light at the proximal end and emits light at the distal end.

6. The dental probe according to claim 5, wherein the distal end of the emitter light guide includes the emitter surface, the distal end being integrally formed with at least one of the second spacer member and/or a pressing member.

7. The dental probe according to claim 5, wherein the light receiver includes a receiver light guide having a proximal end and a distal end, whereby the receiver light guide collects light at the distal end and emits light at the proximal end.

8. The dental probe according to claim 7, wherein the dental probe is a cordless, handheld device.

9. The dental probe according to claim 1, further comprising:
 a second light receiver for detecting scattered light; and
 a sensor configured for determining the distance between the emitting surface and the receiving surface when the dental probe is engaged to the tooth,
 wherein the emitter and receiver light guides are polymeric resin optical fibers or glass fibers; and
 wherein at least one of the light emitter surface or the light receiver surface form part of a member adapted to be removably attached to the dental probe.

10. A member for a dental probe as defined by claim 1, wherein the light emitter surface or the light receiver surface is at least disposable or sterilizable.

11. A dental system comprising the dental probe according to claim 1; and a control unit.

12. The dental system according to claim 11, which further comprises a sensor configured for determining the position of the tooth to be measured, whereby the dental system stores the measured vitality value and position for each measured tooth.

13. The dental system according to claim 11, which comprises a wireless connection between the dental probe and a practice management system for transmitting or exchanging data between the dental probe and the practice management system.

\* \* \* \* \*